(12) United States Patent
Inagaki et al.

(10) Patent No.: US 9,474,195 B2
(45) Date of Patent: Oct. 18, 2016

(54) IMAGE GENERATING APPARATUS AND IMAGE GENERATING METHOD

(75) Inventors: Mitsutaka Inagaki, Chiryu (JP); Ikuo Suzuki, Chiryu (JP); Hiroshi Oike, Chiryu (JP)

(73) Assignee: FUJI MACHINE MFG. CO., LTD., Chiryu-shi (JP)

( * ) Notice: Subject to any disclaimer, the term of this patent is extended or adjusted under 35 U.S.C. 154(b) by 1335 days.

(21) Appl. No.: 13/334,656

(22) Filed: Dec. 22, 2011

(65) Prior Publication Data

US 2012/0162405 A1 Jun. 28, 2012

(30) Foreign Application Priority Data

Dec. 27, 2010 (JP) ................................. 2010-290605

(51) Int. Cl.
H05K 13/00 (2006.01)
H05K 13/08 (2006.01)

(52) U.S. Cl.
CPC .................................... H05K 13/08 (2013.01)

(58) Field of Classification Search
CPC .... H04N 3/239; H04N 13/55; H04N 13/242; H04N 13/37; H05K 13/08
USPC .................................................. 348/42–160
See application file for complete search history.

(56) References Cited

FOREIGN PATENT DOCUMENTS

| CN | 1747647 A | 3/2006 |
|---|---|---|
| JP | A-8-219716 | 8/1996 |
| JP | A-2000-99625 | 4/2000 |
| JP | A-2002-543421 | 12/2002 |
| JP | A-2003-66339 | 3/2003 |
| JP | A-2006-200900 | 8/2006 |
| JP | A-2006-300888 | 11/2006 |
| JP | A-2009-76796 | 4/2009 |
| JP | A-2009-236493 | 10/2009 |
| WO | WO 00/67005 A1 | 11/2000 |

OTHER PUBLICATIONS

Aug. 19, 2014 Office Action issued in Japanese Application No. 2010-290605 (with translation).
Oct. 28, 2014 Office Action issued in Japanese Application No. 2010-290605 (with translation).
Okuda, Kenji et al., "IC Character Reading Machine," *Toshiba Review*, vol. 52, No. 2, pp. 55-58, Feb. 1, 1997 (with abstract).
Masumura, Shigeki, "Writing Technology for Image Processing System and the Prospect," *Eiziojoho Industrial*, vol. 34, No. 1, pp. 29-36, Jan. 2002.
Jun. 8, 2015 Office Action issued in Chinese Application No. 201110457105.6.

*Primary Examiner* — Thai Tran
*Assistant Examiner* — Mishawn Hunter
(74) *Attorney, Agent, or Firm* — Oliff PLC

(57) ABSTRACT

An image generating apparatus includes: a lighting apparatus that emits illumination light to an imaging area where at least a part of an electronic component is located; an imaging apparatus that images the imaging area irradiated with the illumination light; and an image processing apparatus that processes a captured image obtained by the imaging. The image processing apparatus generates a before-adjustment image based on the captured image, generates an adjusted image by adjusting luminance of the before-adjustment image, and generates an optimal image by setting a difference in average luminance between a designated area and a comparison area in the adjusted image largest.

14 Claims, 8 Drawing Sheets

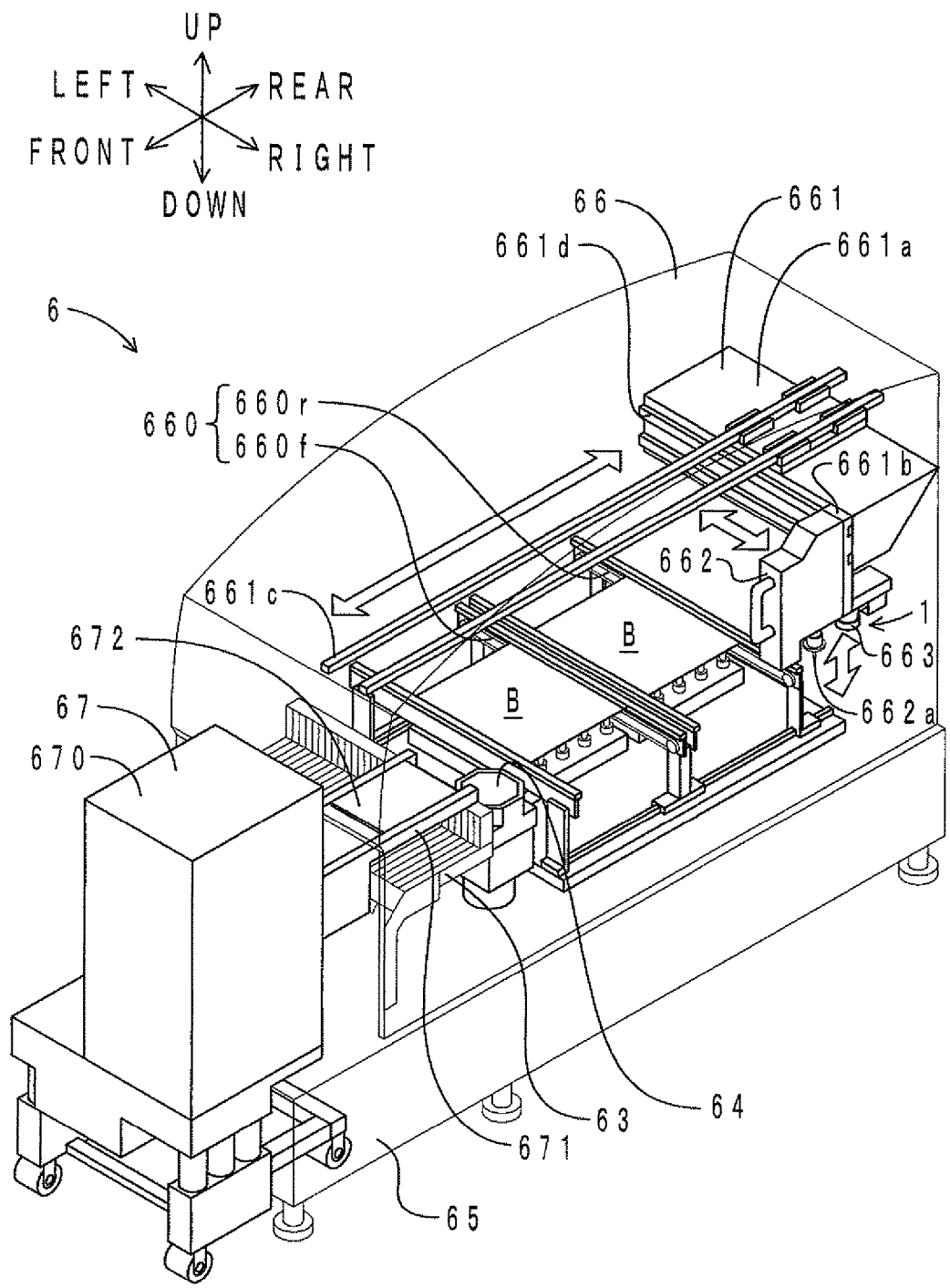
F I G. 7

IMAGE GENERATING APPARATUS AND IMAGE GENERATING METHOD

INCORPORATION BY REFERENCE

The disclosure of Japanese Patent Application No. 2010-290605 filed on Dec. 27, 2011 including the specification, drawings and abstract is incorporated herein by reference in its entirety.

BACKGROUND OF THE INVENTION

1. Field of the Invention

The present invention relates to image generating apparatuses and image generating methods which are used to generate an image for, e.g., inspecting the orientation of an electronic component mounted on a substrate.

2. Description of the Related Art

An inspection apparatus that inspects the orientation of an electronic component placed on a tray is disclosed in Japanese Patent Application Publication No. JP-A-2009-76796. The electronic component has a mark such as a character, a symbol, or a pattern on its upper surface. The mark is typically white, whereas the upper surface of the electronic component is typically black. Thus, average luminance varies between an area with the mark and an area without the mark. Accordingly, the positional relationship between these areas can be determined based on the respective average luminance values of these areas, and the orientation of the electronic component can be determined based on the positional relationship between these areas.

In the inspection apparatus of Japanese Patent Application Publication No. JP-A-2009-76796, however, the accuracy of determining the orientation is low in the case where an image that is used to calculate the average luminance values has low contrast.

Inspection of the orientation is performed not only on an electronic component placed on a tray but also on an electronic component mounted on a substrate. When the image has low contrast, the operator changes lighting conditions (e.g., a lighting color) of a lighting apparatus for an imaging operation, changes the shutter speed of an imaging apparatus, and so forth by trial and error in order to increase the contrast. Accordingly, it takes time to increase the contrast.

The operator needs to be skilled in order to appropriately set the lighting conditions, the lighting color, the shutter speed, and the like. Accordingly, depending on the operator's skill, the inspection apparatus may determine that the orientation of the electronic component is wrong, even if it is actually correct, or the inspection apparatus may determine that the orientation of the electronic component is correct, even if it is actually wrong. That is, if the operator is not so skilled, the probability of such erroneous determination of the inspection apparatus increases. Namely, the accuracy of detecting abnormalities of the electronic component decreases. Moreover, the detection accuracy varies depending on the operator's skill.

SUMMARY OF THE INVENTION

The image generating apparatus and the image generating method according to the present invention were developed in view of the above problems. It is an object of the present invention to provide an image generating apparatus and an image generating method which are capable of automatically generating a high-contrast optimal image from a captured image.

(1) In order to solve the above problems, an image generating apparatus according to a first aspect of the present invention includes: a lighting apparatus that emits illumination light to an imaging area where at least a part of an electronic component is located; an imaging apparatus that images the imaging area irradiated with the illumination light; and an image processing apparatus that processes a captured image obtained by the imaging. The image processing apparatus generates a before-adjustment image based on the captured image, generates an adjusted image by adjusting luminance of the before-adjustment image, and generates an optimal image by setting a difference in average luminance between a designated area and a comparison area that is other than the designated area in the adjusted image largest.

The image generating apparatus according to the first aspect includes the lighting apparatus, the imaging apparatus, and the image processing apparatus. The imaging area of the imaging apparatus is irradiated with the illumination light by the lighting apparatus. At least a part of the electronic component is located in the imaging area. The imaging area is imaged by the imaging apparatus. The before-adjustment image is generated by using as it is the captured image obtained by the imaging, or by performing image processing on the captured image as appropriate. The adjusted image is generated by adjusting the luminance of the before-adjustment image. The optimal image is generated by obtaining the largest difference in average luminance between the designated area and the comparison area in the adjustment image.

Thus, with the image generating apparatus according to the first aspect, a high-contrast optimal image optimal for detection of abnormalities etc. of the electronic component can be automatically generated from the captured image. Accordingly, the optimal image can be obtained in a shorter time as compared to the case where the optimal image is manually obtained by the operator. Moreover, the accuracy of detecting abnormalities of the electronic component is increased regardless of the operator's skill. Moreover, the detection accuracy is less likely to vary, regardless of the operator's skill.

(2) In the configuration according to (1) described above, the image processing apparatus may generate a plurality of selection candidate images based on a plurality of single-color images obtained by decomposing the captured image according to color components, calculate the difference in average luminance between the designated area and the comparison area for each of the selection candidate images, and select a selected image having the largest difference in average luminance from all the selection candidate images, and the before-adjustment image may be the selected image.

According to this configuration, the captured image is decomposed according to the plurality of color components. That is, the plurality of single-color images are generated from the captured image. The plurality of selection candidate images are generated from the plurality of single-color images by using the plurality of single-color images as they are or by synthesizing the plurality of single-color images as appropriate. Each selection candidate image has the designated area and the comparison area. The selected image having the largest difference in average luminance between the areas can be selected from all the selection candidate images by calculating the difference in average luminance between the areas and comparing the differences in average luminance of the selection candidate images with each other. The adjusted image is generated by adjusting the luminance of the selected image. Then, the optimal image is generated by obtaining the largest difference in average luminance between the designated area and the comparison area of the adjusted image. This configuration can increase the contrast of the optimal image.

(3) In the configuration according to (1) or (2) described above, by using a condition obtained in the course of generating the optimal image from the captured image, the image processing apparatus may generate the optimal image from another one of the captured images.

According to this configuration, the condition obtained in image processing performed earlier in time series can be used in image processing to be performed later in the time series. This reduces time required for the later image processing.

As an example, in the case where image processing is performed on a plurality of electronic components of the same kind which are located at the same coordinates, a luminance adjustment condition that is used to generate the adjusted image from the before-adjustment image, a luminance adjustment condition that is used to generate the optimal image from the adjusted image, etc. can be used for both the electronic component that is subjected to the image processing earlier in the time series and the electronic component that is subjected to the image processing later in the time series.

(4) In the configuration according to any one of (1) to (3) described above, the image processing apparatus may generate the adjusted image by adjusting a gain value and an offset value of the before-adjustment image, and the image processing apparatus may generate the optimal image having the largest difference in average luminance, by varying each of the gain value and the offset value of the adjusted image in predetermined increments or decrements and calculating the difference in average luminance between the designated area and the comparison area for each combination of the gain value and the offset value.

FIG. 1A is a conceptual diagram of gain value adjustment, and FIG. 1B shows a conceptual diagram of offset value adjustment. As shown in FIG. 1A, if the magnification of gain value is more than 1, a luminance distribution A2 can be obtained which is wider than a luminance distribution A1 before adjustment. If the magnification of gain value is less than 1, a luminance distribution A3 can be obtained which is narrower than the luminance distribution A1 before adjustment. Thus, the luminance contrast difference can be increased by adjusting the gain value.

As shown in FIG. 1B, adjusting the offset value can shift the position of the luminance distribution without changing its width, as shown by the relationship between the luminance distribution A1 before adjustment and a luminance distribution A4 after adjustment. Thus, addition adjustment of the luminance can be made by adjusting the offset value.

According to this configuration, the adjusted image is generated by adjusting the gain value and the offset value of the before-adjustment image. Then, each of the gain value and the offset value of the adjusted image is varied in the predetermined increments or decrements. Thereafter, the difference in average luminance between the designated area and the comparison area is calculated for each combination of the gain value and the offset value (every time at least one of the gain value and the offset value is varied). The calculated differences in average luminance are compared with each other, and the adjusted image having the largest difference in average luminance is obtained as the optimal image.

According to this configuration, after the before-adjustment image is adjusted by adjusting the gain value and the offset value, the gain value and the offset value are adjusted again so as to obtain the largest difference in average luminance between the designated area and the comparison area. This can increase the contrast between the designated area and the comparison area in the optimal image.

(5) In the configuration according to any one of (1) to (4) described above, the lighting apparatus may have a plurality of illumination units, the plurality of illumination units may have different incident angles of the illumination light on the imaging area from each other, and a plurality of the captured images may be obtained by the imaging apparatus for each of the plurality of illumination units.

If the incident angle of the illumination light is changed, the intensity of light that is reflected from the imaging area to the imaging apparatus is also changed, whereby the contrast of the captured image is changed. According to this configuration, there are the plurality of incident angles of the illumination light, and the number of incident angles is the same as that of the illumination units. Moreover, the captured image is obtained at each of the plurality of incident angles. Thus, a high-contrast captured image can be more easily obtained.

(5-1) In the configuration according to (5) described above, the plurality of illumination units may include an epi-illumination unit that emits the illumination light along a perpendicular line perpendicular to the imaging area, and an oblique-illumination unit that emits the illumination light from a direction crossing the perpendicular line. According to this configuration, the illumination light can be emitted to the imaging area from the perpendicular direction perpendicular to the imaging area and the direction crossing the perpendicular direction.

(6) In the configuration according to any one of (2) to (5) described above, the plurality of color components may be three primary color components of red (R), green (G), and blue (B). According to this configuration, the contrast of the single-color images of any one of R, and B can be increased regardless of the color of the electronic component in the captured image. That is, the image generating apparatus according to this configuration can be adapted to a variety of colors of the electronic component.

(7) In the configuration according to any one of (1) to (6) described above, the electronic component may have a mark by which an orientation of the electronic component can be determined, and the mark may be included in the imaging area and the designated area.

According to this configuration, the orientation inspection can be performed on the electronic component placed on a tray or the electronic component mounted on a substrate, by using the optimal image. Thus, the accuracy of detecting wrong orientation of the electronic component is increased regardless of the operator's skill. Moreover, the detection accuracy is less likely to vary, regardless of the operator's skill.

(8) In the configuration according to (7) described above, the image generating apparatus may further include a display apparatus that displays the optimal image, wherein the image processing apparatus compares the average luminance of the designated area with that of the comparison area of the optimal image before display on the display apparatus, and the image processing apparatus sets the mark of the optimal image to be displayed on the display apparatus to white if the average luminance of the designated area is higher than that of the comparison area, and sets the mark of the optimal image to be displayed on the display apparatus to black if the average luminance of the designated area is lower than that of the comparison area. This configuration can further increase the contrast between the mark in the designated area and the comparison area. Thus, the mark can be more easily recognized.

(9) In order to solve the above problems, an image generating method according to a second aspect of the present invention includes the steps of: generating a before-adjustment image based on a captured image of an imaging area where at least a part of an electronic component is located; adjusting luminance of the before-adjustment image so as to generate an adjusted image; and setting a difference in average luminance between a designated area and a comparison area that is other than the designated area in the adjusted image largest so as to generate an optimal image.

The image generating method according to the second aspect includes the before-adjustment image generation step, the adjusted image generation step, and the optimal image generation step. In the before-adjustment image generation step, the imaging area is first imaged to obtain the captured image. The before-adjustment image is generated by using as it is the captured image obtained by the imaging, or by performing image processing on the captured image as appropriate. The adjusted image is generated by adjusting the luminance of the before-adjustment image. Then, the optimal image is generated by setting the difference in average luminance between the designated area and the comparison area in the adjusted image largest.

Thus, with the image generating method according to the second aspect, the high-contrast optimal image optimal for detection of abnormalities etc. of the electronic component can be automatically generated from the captured image. Accordingly, the optimal image can be obtained in a shorter time as compared to the case where the optimal image is manually obtained by the operator. Moreover, the accuracy of detecting abnormalities of the electronic component is increased regardless of the operator's skill. Moreover, the detection accuracy is less likely to vary, regardless of the operator's skill.

(10) In the configuration according to (9) described above, the before-adjustment image generation step may include the steps of: decomposing the captured image according to color components to generate a plurality of single-color images, and generating a plurality of selection candidate images based on the plurality of single-color images; and calculating the difference in average luminance between the designated area and the comparison area for each of the selection candidate images, and selecting a selected image having the largest difference in average luminance from the selection candidate images. The before-adjustment image may be the selected image.

According to this configuration, the before-adjustment image generation step includes the selection candidate image generation step and the image selection step. In the selection candidate image generation step, the captured image is first decomposed according to the color components to generate the plurality of single-color images. Next, the plurality of selection candidate images are generated from the plurality of single-color images by using the plurality of single-color images as they are, or by synthesizing the plurality of single-color images as appropriate. In the image selection step, the difference in average luminance between the designated area and the comparison area is first calculated for each of the selection candidate images. Then, the selected image having the largest difference in average luminance is selected from the selection candidate images. This configuration can increase the contrast of the optimal image.

(11) In the configuration according to (9) or (10) described above, the image generating method may further include the step of, after the optimal image generation step, generating the optimal image from another one of the captured images by using a condition obtained in the course from the before-adjustment image generation step to the optimal image generation step.

According to this configuration, the condition obtained in image processing performed earlier in time series can be used in image processing to be performed later in the time series. This reduces the time required for the later image processing.

As an example, in the case where image processing is performed on a plurality of electronic components of the same kind which are located at the same coordinates, a luminance adjustment condition that is used to generate the adjusted image from the before-adjustment image in the adjusted image generation step, a luminance adjustment condition that is used to generate the optimal image from the adjusted image in the optimal image generation step, etc. can be used for both the electronic component that is subjected to the image processing earlier in the time series and the electronic component that is subjected to the image processing later in the time series.

(12) In the configuration according to any one of (9) to (11) described above, in the adjusted image generation step, the adjusted image may be generated by adjusting a gain value and an offset value of the before-adjustment image, and in the optimal image generation step, the optimal image having the largest difference in average luminance may be generated by varying each of the gain value and the offset value of the adjusted image in predetermined increments or decrements and calculating the difference in average luminance between the designated area and the comparison area for each combination of the gain value and the offset value.

In the adjusted image generation step, the adjusted image is generated by adjusting the gain value and the offset value of the before-adjustment image. In the optimal image generation step, each of the gain value and the offset value of the adjusted image is varied in the predetermined increments or decrements. Thereafter, the difference in average luminance between the designated area and the comparison area is calculated for each combination of the gain value and the offset value (every time at least one of the gain value and the offset value is varied). The calculated differences in average luminance are compared with each other, and the adjusted image having the largest difference in average luminance is obtained as the optimal image.

According to this configuration, after the before-adjustment image is adjusted by adjusting the gain value and the offset value, the largest difference in average luminance between the designated area and the comparison area is obtained by adjusting the gain value and the offset value again. This can increase the contrast between the designated area and the comparison area in the optimal image.

(13) In the configuration according to any one of (9) to (12) described above, the electronic component may have a mark by which an orientation of the electronic component can be determined, and the mark may be included in the imaging area and the designated area.

According to this configuration, the orientation inspection can be performed on the electronic component placed on a tray or the electronic component mounted on a substrate, by using the optimal image. Thus, the accuracy of detecting wrong orientation of the electronic component is increased regardless of the operator's skill. Moreover, the detection accuracy is less likely to vary, regardless of the operator's skill.

(14) In the configuration according to (13) described above, in the optimal image generation step, the average luminance of the designated area may be compared with that of the comparison area in the optimal image, the mark of the optimal image may be set to white if the average luminance of the designated area is higher than that of the comparison area, and the mark of the optimal image may be set to black if the average luminance of the designated area is lower than that of the comparison area. This configuration can further increase the contrast between the mark in the designated area and the comparison area. Thus, the mark can be more easily recognized.

According to the first and second aspects of the present invention, an image generating apparatus and an image generating method can be provided which are capable of automatically generating a high-contrast optimal image from a captured image.

BRIEF DESCRIPTION OF THE DRAWINGS

FIG. 7 is a perspective view of an electronic component mounting machine incorporating an image generating apparatus according to an embodiment of the present invention.

DETAILED DESCRIPTION OF THE EMBODIMENTS

An embodiment of an image generating apparatus and an image generating method according to the present invention will be described below.

<Layout and Configuration of Substrate Appearance Inspection Machine>

Figure 1A:
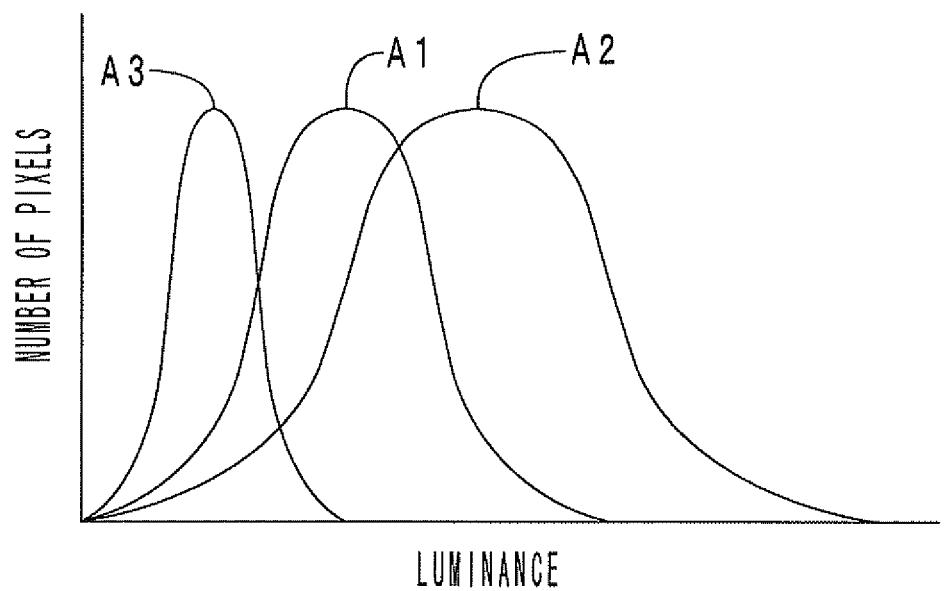
FIG. 1A is a conceptual diagram of gain value adjustment.
Figure 1B:
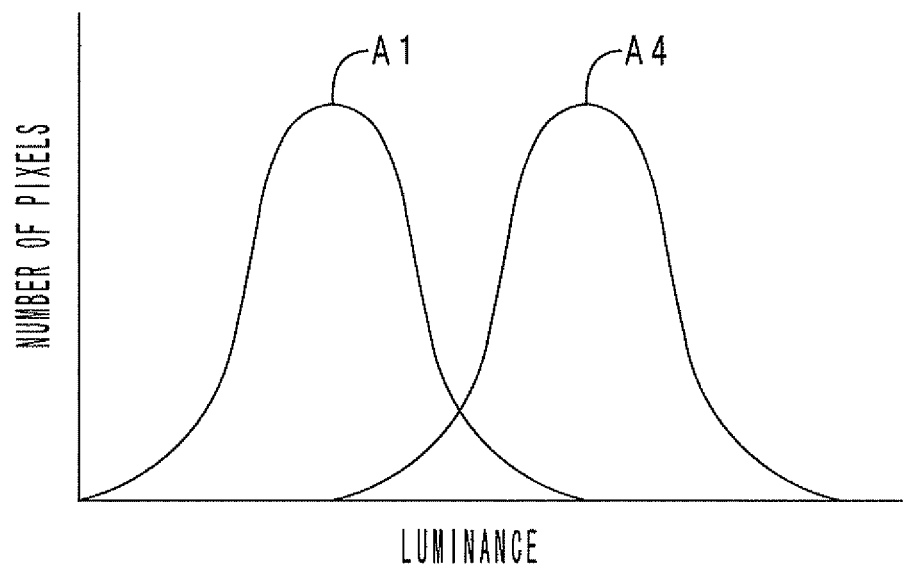
FIG. 1B is a conceptual diagram of offset value adjustment.
Figure 2:
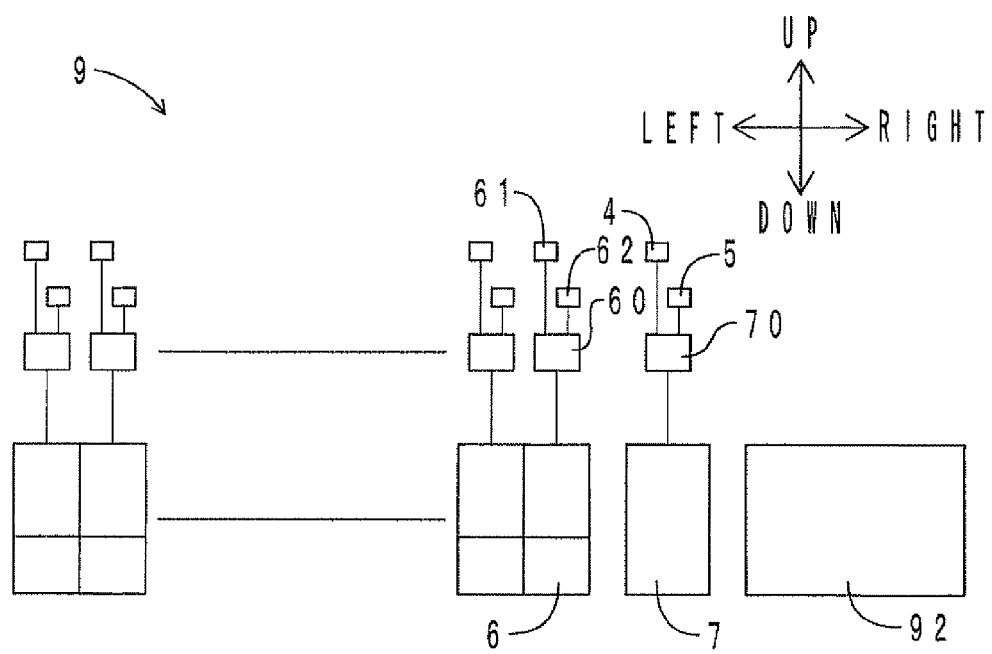
FIG. 2 is a schematic diagram showing a substrate production line incorporating a substrate appearance inspection machine according to an embodiment of the present invention.

First, the layout of a substrate appearance inspection machine incorporating an image generating apparatus of the present embodiment will be described below. FIG. 2 is a schematic diagram of a substrate production line having the substrate appearance inspection machine disposed therein. As shown in FIG. 2, a substrate production line 9 includes a plurality of electronic component mounting machines 6, a substrate appearance inspection machine 7, and a reflow furnace 92, sequentially from left (upstream) to right (downstream). The substrate appearance inspection machine 7 is interposed between the most downstream one of the electronic component mounting machines 6 and the reflow furnace 92.

A multiplicity of electronic components are mounted stepwise on a substrate that is transferred on the substrate production line 9, by the plurality of electronic component mounting machines 6. The substrate appearance inspection machine 7 inspects the mounting states of the electronic components on the substrate. The reflow furnace 92 melts cream solder interposed between the substrate and the electronic components to solder the electronic components to the substrate.

Figure 3:
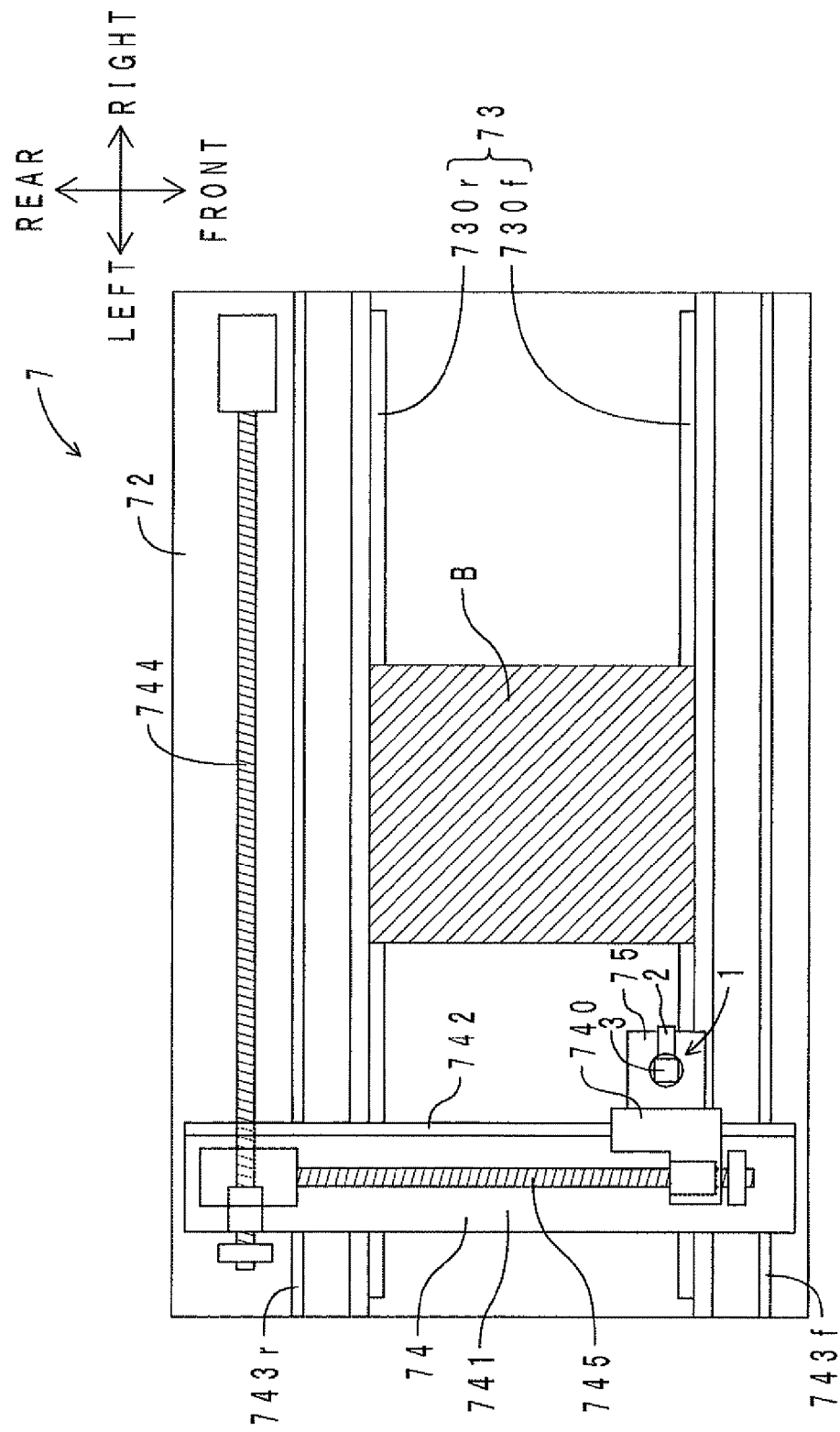
FIG. 3 is a top view of the substrate appearance inspection machine.

The configuration of the substrate appearance inspection machine 7 will be described below. FIG. 3 is a top view of the substrate appearance inspection machine 7. Note that a substrate B is shown hatched in FIG. 3. As shown in FIG. 3, the substrate appearance inspection machine 7 includes a base 72, a substrate transfer apparatus 73, an XY robot 74, an inspection head 75, a control apparatus 70 (see FIG. 2), an image processing apparatus 4 (see FIG. 2), and a display apparatus 5 (see FIG. 2).

The substrate transfer apparatus 73 is disposed on the upper surface of the base 72. The substrate transfer apparatus 73 includes a pair of front and rear conveyor belts 730f, 730r. The position and width of the substrate transfer apparatus 73 in the front-rear direction can be changed according to the position and width of transfer portions 660f, 660r of a substrate transfer apparatus 660 of the electronic component mounting machine 6 described later in the front-rear direction (see FIG. 7). The substrate B is transferred from left to right by the conveyor belts 730f, 730r. The conveyor belts 730f, 730r have a function as a substrate transfer device that transfers the substrate.

The "X direction," the "Y direction," and the "Z direction" correspond to the left-right direction, the front-rear direction, and the up-down direction, respectively. The XY robot 74 includes a Y-direction slider 740, an X-direction slider 741, a pair of upper and lower Y-direction guide rails 742, a pair of front and rear X-direction guide rails 743f, 743r, an X-direction movement ball screw portion 744, and a Y-direction movement ball screw portion 745.

The pair of front and rear X-direction guide rails 743f, 743r are disposed on the upper surface of the base 72 such that the substrate transfer apparatus 73 is interposed therebetween in the front-rear direction. The X-direction slider 741 is attached to the pair of front and rear X-direction guide rails 743f, 743r so as to be slidable in the left-right direction. The X-direction slider 741 is driven by the X-direction movement ball screw portion 744 attached to the base 72. The pair of upper and lower Y-direction guide rails 742 are disposed on the X-direction slider 741. The Y-direction slider 740 is attached to the pair of upper and lower Y-direction guide rails 742 so as to be slidable in the front-rear direction. The Y-direction slider 740 is driven by the Y-direction movement ball screw portion 745 attached to the X-direction slider 741.

Figure 4:
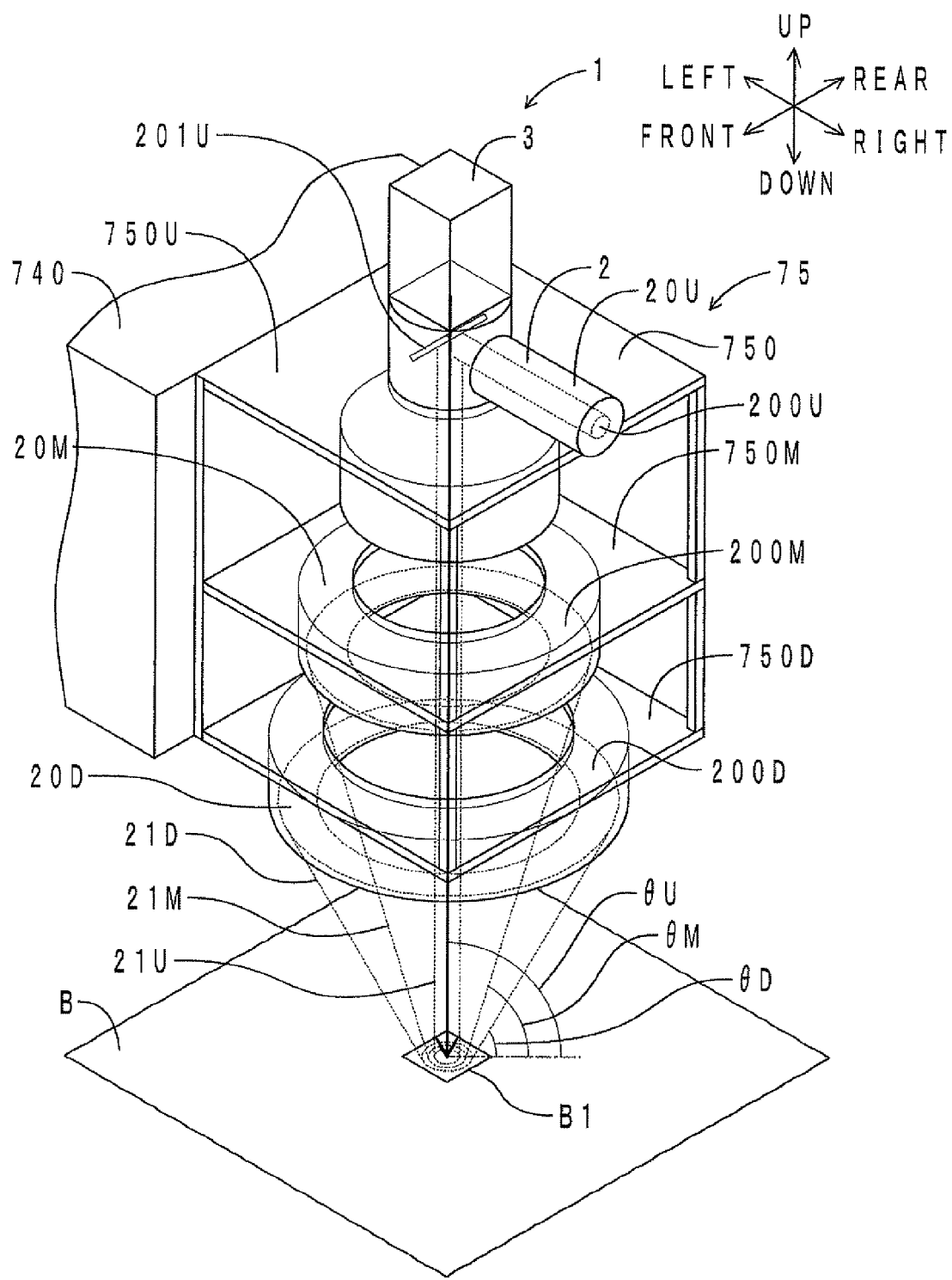
FIG. 4 is a perspective view of a portion near an inspection head of the substrate appearance inspection machine.

The inspection head 75 is attached to the right surface of the Y-direction slider 740. Thus, the inspection head 75 is movable in the front-rear and left-right directions by the XY robot 74. FIG. 4 is a perspective view of a portion near the inspection head 75 of the substrate appearance inspection machine 7. As shown in FIG. 4, the inspection head 75 includes a frame 750, a lighting apparatus 2, and an imaging apparatus 3. The frame 750 includes three-stage brackets, namely upper, middle, and lower brackets 750U, 750M, and 750D. Each of the brackets 750U, 750M, 750D is provided, in the center thereof, with a hole that allows light to pass therethrough.

The lighting apparatus 2 includes an epi-illumination unit 20U, an upper oblique-illumination unit 20M, and a lower oblique-illumination unit 20D. The epi-illumination unit 20U, the upper oblique-illumination unit 20M, and the lower oblique-illumination unit 20D are conceptually included in the "illumination unit" of the present invention.

The epi-illumination unit 20U is attached to the upper bracket 750U. The epi-illumination unit 20U includes a light source 200U, a half mirror 201U, and an optical system (not shown). As shown by dotted lines in FIG. 4, light (illumination light) 21U emitted from the light source 200U is converted to parallel light by the optical system having a lens and the like. The emitted light 21U travels leftward, changes its direction by 90° at the half mirror 201U, and travels downward. Thus, an imaging area B1 on the upper surface of the substrate B is irradiated with the emitted light 21U from the direction directly above the imaging area B1. An incident angle θU of the emitted light 21U on the imaging area B1 is 90°.

The upper oblique-illumination unit 20M is attached to the middle bracket 750M. The upper oblique-illumination unit 20M includes a ring-shaped light source 200M. As shown by dotted lines in FIG. 4, the imaging area B1 on the upper surface of the substrate B is irradiated with upper oblique light (illumination light) 21M emitted from the light source 200M from the direction of an incident angle θM (<θU).

The lower oblique-illumination unit 20D is attached to the lower bracket 750D. The lower oblique-illumination unit 20D includes a ring-shaped light source 200D. As shown by dotted lines in FIG. 4, the imaging area B1 on the upper surface of the substrate B is irradiated with lower oblique light (illumination light) 21D emitted from the light source 200M from the direction of an incident angle θD (<θM).

The light sources 200U, 200M, and 200D are white light-emitting diodes (LEDs). Thus, each of the light sources 200U, 200M, and 200D has all of three primary color components of red (R), green (G), and blue (B). The imaging apparatus 3 is attached to the upper bracket 750U. The imaging apparatus 3 is a charge coupled device (CCD) area sensor. The imaging apparatus 3 has an imaging plane on which a multiplicity of light receiving elements are arranged two-dimensionally. The imaging apparatus 3 images the imaging area B1 from the direction directly above the imaging area B1.

The control apparatus 70 shown in FIG. 2 is capable of controlling in an integrated manner the substrate transfer apparatus 73, the XY robot 74, and the inspection head 75, which are described above. The control apparatus 70 is electrically connected to the image processing apparatus 4 and the display apparatus 5.

An image generating apparatus 1 of the present embodiment is incorporated in the substrate appearance inspection machine 7. The image generating apparatus 1 includes the lighting apparatus 2, the imaging apparatus 3, the image processing apparatus 4, and the display apparatus 5, out of the constituent members of the substrate appearance inspection machine 7.

<Movement of Substrate Appearance Inspection Machine and Image Generating Apparatus During Production of Substrate>

Movement of the substrate appearance inspection machine 7 and the image generating apparatus 1 during production of the substrate will be described below. As shown in FIG. 2, the substrate on which electronic components have been mounted passes through the substrate appearance inspection machine 7. The mounting state of the electronic components on the substrate is inspected here.

Figure 5:
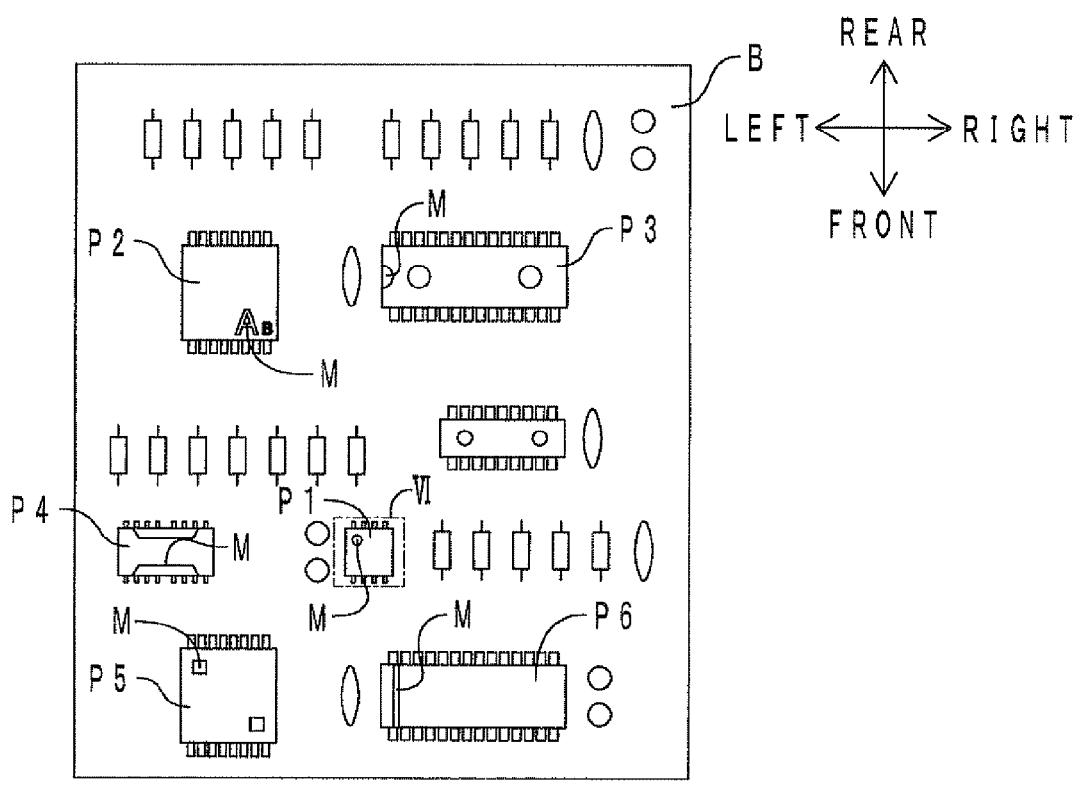
FIG. 5 is a top view of a substrate on which electronic components have been mounted.

FIG. 5 is a top view of the substrate on which the electronic components have been mounted. As shown in FIG. 5, various electronic components P1 to P6 have been mounted on the substrate B. All the electronic components P1 to P6 are imaged by the imaging apparatus 3 shown in FIG. 4 in a predetermined order. Thus, the electronic components P1 to P6 are inspected for positional displacement or orientation displacement, or the electronic components P1 to P6 are inspected to see if there is any component missing.

An example in which the orientation of any one of the electronic components (the electronic component P1 in this example) is inspected will be described below. In the orientation inspection, the electronic component P1 is inspected to check if the orientation of the electronic component P1 matches a predetermined orientation (e.g., to check if the electronic component P1 is properly mounted on the substrate B and not rotated 90° or 180°).

First, the inspection head 75 shown in FIGS. 3 and 4 is moved to the position directly above the electronic component P1 so that the electronic component P1 is located in the imaging area B1. Next, the epi-illumination unit 20U, the upper oblique-illumination unit 20M, and the lower oblique-illumination unit 20D, which are shown in FIG. 4, are sequentially turned on, and the imaging area B1 is imaged by the imaging apparatus 3 shown in FIG. 4 when each illumination unit is turned on. That is, a total of three images are obtained. Then, the three images are processed by the image processing apparatus 4 shown in FIG. 2. Subsequently, the orientation of the electronic component P1 is inspected.

If the substrate B is the first substrate that has been transferred, an optimal image of the imaging area B1 is generated through a before-adjustment image generation step (a selection candidate image generation step and an image selection step), an adjusted image generation step, and an optimal image generation step of an image generating method described below. Then, the orientation inspection is performed by using the optimal image. On the other hand, if the substrate B is the second or subsequent one of the substrates transferred, an optimal image of the imaging area B1 is generated only through a condition utilization step of the image generating method described below. Then, the orientation inspection is performed by using the optimal image.

The optimal image is displayed on the display apparatus (display) 5. Whether the orientation of the electronic component is correct or not is automatically determined based on the average luminance of the optimal image, as described below. After inspection of all the electronic components P1 to P6 shown in FIG. 5 is completed, the inspected substrate is carried from the substrate appearance inspection machine 7 into the reflow furnace 92, as shown in FIG. 2.

<Image Generating Method>

Figure 6:
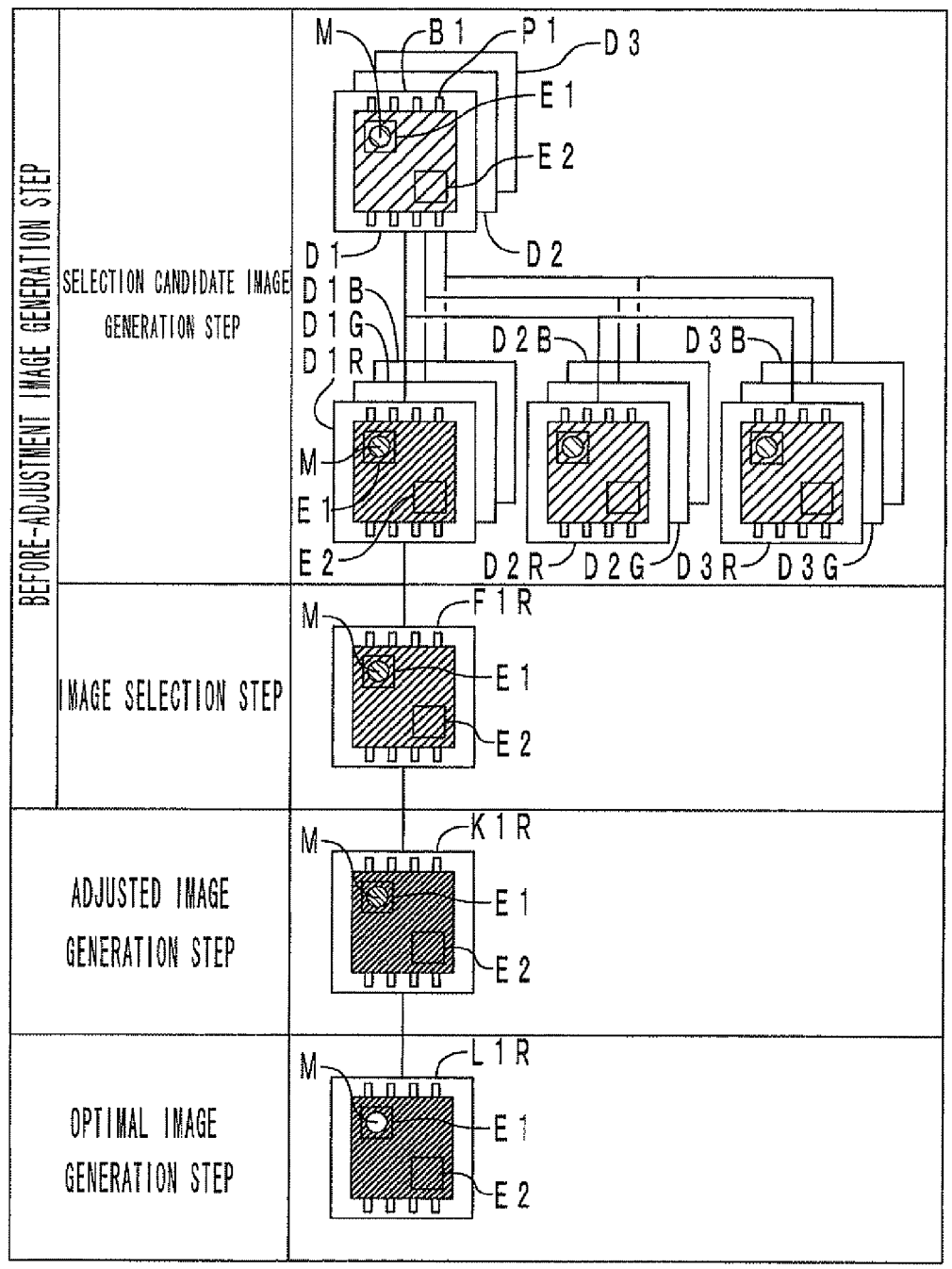
FIG. 6 is a schematic diagram illustrating an image generating method according to an embodiment of the present invention.

The image generating method of the present embodiment will be described below. An example will be described below in which an optimal image is generated from captured images of the electronic component P1 located in a region VI shown in FIG. 5. FIG. 6 is a schematic diagram illustrating the image generating method of the present embodiment. As shown in FIG. 6, the image generating method of the present embodiment includes the before-adjustment image generation step, the adjusted image generation step, the optimal image generation step, and the condition utilization step (not shown).

[Before-Adjustment Image Generation Step]

This step includes the selection candidate image generation step and the image selection step.

(Selection Candidate Image Generation Step)

In this step, the inspection head 75 shown in FIGS. 3 and 4 is first moved by the control apparatus 70 shown in FIG. 2 so that the electronic component P1 shown in FIG. 5 is located in the imaging area B1 shown in FIG. 4.

Next, the epi-illumination unit 20U shown in FIG. 4 is turned on by the control apparatus 70 shown in FIG. 2. Then, with the emitted light 21U being incident on the imaging area B1 from directly thereabove, the imaging area B1 is imaged by the imaging apparatus 3. Thereafter, the epi-illumination unit 20U shown in FIG. 4 is turned off and the upper oblique-illumination unit 20M is turned on by the control apparatus 70 shown in FIG. 2. Subsequently, with the upper oblique light 21M being incident on the imaging area B1 from an upper peripheral level, the imaging area B1 is imaged by the imaging apparatus 3. Then, the upper oblique-illumination unit 20M shown in FIG. 4 is turned off and the lower oblique-illumination unit 20D is turned on by the control apparatus 70 shown in FIG. 2. Subsequently, with the lower oblique light 21D being incident on the imaging area B1 from a lower peripheral level, the imaging area B1 is imaged by the imaging apparatus 3. In this manner, three captured images D1 to D3 are obtained at different incident angles of the illumination light, as shown in FIG. 6.

A designated area E1 and a comparison area E2 are set in each of the captured images D1 to D3. The shape and size (the number of pixels: 8 bits) of the designated area E1 are the same as those of the comparison area E2. A circular mark M is included in the designated area E1

The three captured images D1 to D3 are color images. Each of the captured images D1 to D3 is decomposed into three primary color components of R, and B. These primary color components are turned into data, and transmitted from the imaging apparatus 3 to the image processing apparatus 4 shown in FIG. 2. In the image processing apparatus 4, three single-color images D1R, D1G, and D1B of the three primary colors R, G, and B are generated from the captured image D1, three single-color images D2R, D2G, and D2B of the three primary colors R, G, and B are generated from the captured image D2, and three single-color images D3R, D30, and D3B of the three primary colors R, G, and B are generated from the captured image D3. A total of nine single-color images D1R, D1G, D1B, D2R, D2G, D2B, D3R, D3G, and D3B are generated in this manner. The nine single-color images D1R, D1G, D1B, D2R, D2G, D2B, D3R, D3G, and D3B are used as they are as selection candidate images.

(Image Selection Step)

In this step, the difference in average luminance between the designated area E1 and the comparison area E2 is calculated for each of the nine single-color images D1R, D1G, D1B, D2R, D2G, D2B, D3R, D3G, and D3B.

Specifically, the luminance of each pixel in the designated area E1 is detected, and a sum of the respective luminance values of the pixels is divided by the number of pixels in the designated area E1. Similarly, the luminance of each pixel in the comparison area E2 is detected, and a sum of the respective luminance values of the pixels is divided by the number of pixels in the comparison area E2. The average luminance of the designated area E1 and the average luminance of the comparison area E2 are calculated in this manner.

Next, the difference in average luminance between the designated area E1 and the comparison area E2 is calculated for each of the nine single-color images D1R, D1G, D1B, D2R, D2G; D2B, D3R, D3G, and D3B. Then, the single-color image (the single-color image D1R in this example) having the largest difference in average luminance is selected as a selected image F1R.

[Adjusted Image Generation Step]

In this step, a lookup table is first created. Specifically, the range of a gain value J is set to 0.00 to 255.00. The range of an offset value I is set to −255 to 255. A brightness reference value H is calculated by the following expression (1).

$$H = 127.5 - I \times 0.5 \qquad (1)$$

Brightness J after conversion is calculated by the following expression (2).

$$J = ((x - H) \times J + H + 0.5) + I \qquad (2)$$

The lookup table is created by increasing a variable x in the expression (2) in increments of 1 from 0 to 255. Note that J is set to 0 (J=0) when the brightness J after conversion is lower than 0, and J is set to 255 (J=255) when the brightness J after conversion is higher than 255.

Then, image conversion is performed on the selected image F1R based on the lookup table thus created. Thus, an adjusted image K1R is generated which has higher contrast between the designated area E1 and the comparison area E2 than the selected image F1R.

[Optimal Image Generation Step]

In this step, the offset value for the adjusted image K1R is varied in increments or decrements of 10 from −200 to 200 while increasing the gain value in increments of 0.20 from 0.00 to 255.00. The difference in average luminance between the designated area E1 and the comparison area E2 is calculated for each combination of the gain value and the offset value. Note that the difference in average luminance is calculated by a method similar to that in the image selection step.

For example, if the gain value is 1.00 and the offset value is varied from −200 to 200, (gain value, offset value) is (1.00, −200), (1.00, −190), (1.00, −180), . . . (1.00, 180), (1.00, 190), and (1.00, 200). The difference in average luminance between the designated area E1 and the comparison area E2 is calculated for each combination of the gain value and the offset value.

If the gain value is 1.20 and the offset value is varied from −200 to 200, (gain value, offset value) is (1.20, −200), (1.20, −190), (1.20, −180), . . . (1.20, 180), (1.20, 190), and (1.20, 200). The difference in average luminance between the designated area E1 and the comparison area E2 is calculated for each combination of the gain value and the offset value.

Then, the combination of the gain value and the offset value is selected which has the largest difference in average luminance. Note that if there are a plurality of combinations yielding the largest difference in average luminance, the combination having the smallest gain value is selected. The reason for this is that the larger the gain value is, the greater the influence of the individual differences is.

Thereafter, image conversion is performed on the adjusted image K1R by using the selected combination of the gain value and the offset value, thereby generating an optimal image L1R having higher contrast between the designated area E1 and the comparison area E2 than the adjusted image K1R.

Subsequently, the average luminance is compared between the designated area E1 and the comparison area E2 of the optimal image L1R by using the combination of the gain value and the offset value that yields the largest difference in average luminance. If the average luminance of the designated area E1 is higher than that of the comparison area E2, the mark M of the optimal image L1R is set to white. On the other hand, if the average luminance of the designated area E1 is lower than that of the comparison area E2, the mark M of the optimal image L1R is set to black.

The optimal image L1R thus having the black or white mark M is displayed on the display apparatus 5 shown in FIG. 2. Whether the orientation of the electronic component is correct or not is automatically determined. Specifically, as described in Japanese Patent Application Publication No. JP-A-2009-76796, the image processing apparatus 4 compares the average luminance of the designated area E1 with that of the comparison area E2 in the optimal image L1R shown in FIG. 6. It is herein assumed that the orientation shown in FIG. 6 is a correct mounting orientation of the electronic component P1. When it is determined, based on the comparison result, that the average luminance in the designated area E1 is higher than that of the comparison area E2, this means that the mark M having high luminance is present in the designated area E1. Thus, it is determined that the orientation of the electronic component P1 is correct. On the contrary, when it is determined that the average luminance of the designated area E1 is lower than that of the comparison area E2, this means that the mark M having high luminance is present in the comparison area E2. Thus, it is determined that the orientation of the electronic component P1 is wrong.

The series of steps described above, namely the selection candidate image generation step, the image selection step, the adjusted image generation step, and the optimal image generation step, are performed on all of the electronic components P1 to P6 shown in FIG. 5. After inspection of all the electronic components P1 to P6 is completed, the inspected substrate is carried from the substrate appearance inspection machine 7 into the reflow furnace 92, as shown in FIG. 2.

[Condition Utilization Step]

As shown in FIG. 2, if the inspected substrate is carried into the reflow furnace 92, the subsequent substrate to be inspected is transferred from the electronic component mounting machine 6 into the substrate appearance inspection machine 7. In this step, the electronic components on the new substrate are inspected by utilizing as they are the conditions obtained by the series of steps described above, namely the selection candidate image generation step, the image selection step, the adjusted image generation step, and the optimal image generation step.

Specifically, the new substrate is of the same kind as the inspected substrate. That is, as shown in FIG. 5, the same electronic components P1 to P6 are mounted at the same coordinates on both the new substrate B and the inspected substrate B. Thus, the conditions for the electronic component P1 on the inspected substrate B can be used as they are for the electronic component P1 on the new substrate B. The same applies to the electronic components P2 to P6.

As an example, inspection of the orientation of the electronic component P1 on the new substrate B will be described below by comparing with the inspection of the orientation of the electronic component P1 on the inspected substrate B described above.

(Selection Candidate Image Generation Step)

The only one captured image D1 is obtained in this step. That is, the imaging conditions of the captured image D1 are utilized which have been set in the selection candidate image generation step performed on the inspected substrate. The imaging conditions are conceptually included in the "condition" in the present invention. Specifically, the epi-illumination unit 20U shown in FIG. 4 is turned on, and the imaging area B1 is imaged by using the imaging apparatus 3.

The reason why the only one captured image D1 is obtained is that, as shown in FIG. 6, it has already been known from the result of the selection candidate image generation step and the image selection step performed on the inspected substrate that the single-color image D1R obtained from the captured image D1 is going to be selected as the selected image F1R.

(Image Selection Step)

In this step, the single-color image D1R is selected as it is as the selected image F1R.

(Adjusted Image Generation Step)

The lookup table created in the adjusted image generation step performed on the inspected substrate is used in this step. The lookup table is conceptually included in the "condition" in the present invention. That is, image conversion is performed on the selected image F1R by using the lookup table. Thus, the adjusted image K1R is generated which has higher contrast between the designated area E1 and the comparison area E2 than the selected image F1R.

(Optimal Image Generation Step)

In this step, a combination of the gain value and the offset value that yields the largest difference in average luminance is used. This combination is the combination obtained in the optimal image generation step performed on the inspected substrate. The combination of the gain value and the offset value that yields the largest difference in average luminance is conceptually included in the "condition" in the present invention. That is, image conversion is performed on the adjusted image K1R by using this combination of the gain value and the offset value. Thus, the optimal image L1R is generated which has higher contrast between the designated area E1 and the comparison area E2 than the adjusted image K1R.

Then, the optimal image L1R having the white mark M is displayed on the display apparatus 5 shown in FIG. 2. Thus, whether the orientation of the electronic component is correct or not is automatically determined.

The condition utilization step is performed on all of the electronic components P1 to P6 shown in FIG. 5. After inspection of all the electronic components P1 to P6 is completed, the inspected substrate is carried from the substrate appearance inspection machine 7 into the reflow furnace 92, as shown in FIG. 2. When the inspected substrate is carried into the reflow furnace 92, the subsequent substrate to be inspected is transferred from the electronic component mounting machine 6 to the substrate appearance inspection machine 7. The condition utilization step is also performed on this substrate. Thus, the condition utilization step is sequentially repeatedly performed on the substrates of the same kind.

<Operations and Effects>

Operations and effects of the image generating apparatus 1 and the image generating method according to the present embodiment will be described below. According to the image generating apparatus 1 and the image generating method of the present embodiment, as shown in FIG. 6, the high-contrast optimal image L1R that is optimal for detection of abnormalities etc. of the electronic components P1 to P6 can be automatically generated from the captured images D1 to D3. Thus, the optimal image L1R can be obtained in a shorter time as compared to the case where the optimal image L1R is manually obtained by the operator. Moreover, the accuracy of detecting abnormalities of the electronic components P1 to P6 is increased regardless of the operator's skill. Moreover, the detection accuracy is less likely to vary, regardless of the operator's skill.

According to the image generating apparatus 1 and the image generating method of the present embodiment, the conditions obtained when the selection candidate image generation step, the image selection step, the adjusted image generation step, and the optimal image generation step are performed on the first substrate can be used as they are for the second and subsequent substrates. Namely, the condition utilization step can be repeatedly performed on the second and subsequent substrates.

That is, the conditions obtained in the orientation inspection of the electronic components P1 to P6 on the first substrate (the number of captured images D1 and the imaging conditions in the selection candidate image generation step, the lookup table in the adjusted image generation step, the combination of the gain value and the offset value that yields the largest difference in average luminance in the optimal image generation step, etc.) can be utilized as they are in the orientation inspection of the electronic components P1 to P6 on the second and subsequent substrates. This reduces the time required for the image processing and therefore for the orientation inspection of the electronic components P1 to P6.

According to the image generating apparatus 1 and the image generating method of the present embodiment, as shown in FIG. 6, the gain value and the offset value are adjusted in the adjusted image generation step so as to generate the adjusted image K1R from the selected image F1R. Moreover, in the optimal image generation step, the gain value and the offset value are adjusted again so as to generate the optimal image L1R from the adjusted image K1R. This can increase the contrast between the designated area E1 and the comparison area E2 in the optimal image L1R.

According to the image generating apparatus 1 and the image generating method of the present embodiment, as shown in FIG. 4, the lighting apparatus 2 includes the epi-illumination unit 20U, the upper oblique-illumination unit 20M, and the lower oblique-illumination unit 20D. The incident angle θU of the light 21U emitted from the epi-illumination unit 20U, the incident angle θM of the upper oblique light 21M from the upper oblique-illumination unit 20M, and the incident angle θD of the lower oblique light 21D from the lower oblique-illumination unit 20D are different from each other. The captured image D1 shown in FIG. 6 is captured by the imaging apparatus 3 when the imaging area B1 is irradiated with the emitted light 21U. The captured image D2 shown in FIG. 6 is captured by the imaging apparatus 3 when the imaging area B1 is irradiated with the upper oblique light 21M. The captured image D3 shown in FIG. 6 is captured by the imaging apparatus 3 when the imaging area B1 is irradiated with the lower oblique light 21D. Thus, the contrast varies among the captured images D1 to D3. This makes it easier to obtain the captured image D1 to D3 having high contrast.

According to the image generating apparatus 1 and the image generating method of the present embodiment, the single-color images D1R, D1G, D1B, D2R, D2G, D2B, D3R, D3G, and D3B of the three primary colors R, G, and B are generated, as shown in FIG. 6. Thus, the contrast of the single-color images D1R, D1G, D1B, D2R, D2G, D2B, D3R, D3G, D3B of any one of R, G, and B can be increased regardless of the color of the electronic components P1 to P6 in the captured images D1 to D3. That is, the image generating apparatus 1 and the image generating method of the present embodiment can be adapted to a variety of colors of the electronic components P1 to P6.

According to the image generating apparatus 1 and the image generating method of the present embodiment, as shown in FIG. 2, the mark M in the optimal image L1R that is displayed on the display apparatus 5 is set to white or black according to the average luminance values of the designated area E1 and the comparison area E2. This can further increase the contrast between the mark M in the designated area E1 and the comparison area E2. Thus, the mark M can be more easily recognized.

<Others>

The embodiment of the image generating apparatus and the image generating method according to the present invention is described above. However, embodiments are not particularly limited to the one described above. It will be apparent to those skilled in the art that various modifications or variations may be made without departing from the scope of the invention.

Although the image generating apparatus 1 is incorporated in the substrate appearance inspection machine 7 in the above embodiment, the image generating apparatus 1 may be incorporated in the electronic component mounting machine 6. FIG. 7 is a perspective view of the electronic component mounting machine 6 incorporating the image generating apparatus according to the embodiment of the present invention. The electronic component mounting machine 6 includes a base 65, a module 66, a tray unit 67, a device pallet 63, a control apparatus 60 (see FIG. 2), an image processing apparatus 61 (see FIG. 2), and a display apparatus 62 (see FIG. 2).

The module 66 is detachably provided on the upper surface of the base 65. The module 66 includes the substrate transfer apparatus 660, an XY robot 661, a mount head 662, a mark camera 663, a part camera 64, and a lighting apparatus (not shown). The substrate transfer apparatus 660 includes the pair of front and rear transfer portions 660f, 660r. The mark camera 663 is conceptually included in the "imaging apparatus" of the present invention.

Each of the transfer portions 660f, 660r includes a pair of conveyor belts. Each of the transfer portions 660f, 660r is capable of transferring the substrate B. The XY robot 661 includes a Y-direction slider 661a, an X-direction slider 661b, a pair of right and left Y-direction guide rails 661c, and a pair of upper and lower X-direction guide rails 661d. The pair of right and left Y-direction guide rails 661c are disposed on the upper surface of the inner space of a housing of the module 66. The Y-direction slider 661a is attached to the pair of right and left Y-direction guide rails 661c so as to be slidable in the front-rear direction. The pair of upper and lower X-direction guide rails 661d are disposed on the front surface of the Y-direction slider 661a. The X-direction slider 661b is attached to the pair of upper and lower X-direction guide rails 661d so as to be slidable in the left-right direction.

The mount head 662 is attached to the X-direction slider 661b. Thus, the mount head 662 is movable in the front-rear and left-right directions by the XY robot 661. A suction nozzle 662a is attached to a lower portion of the mount head 662. The suction nozzle 662a is movable downward with respect to the mount head 662.

The mark camera 663 and the lighting apparatus (white LED), together with the mount head 662, are attached to the X-direction slider 661. The mark camera 663 and the lighting apparatus (white LED) are movable in the front-rear and left-right directions by the XY robot 661. The mark camera 663 is capable of imaging the substrate B and an alignment mark on the electronic component. The lighting apparatus is capable of emitting illumination light to an imaging area of the mark camera 663.

The part camera 64 is disposed in front of the transfer portion 660*f*. The suction nozzle 662*a* (i.e., the mount head 662) that has picked up the electronic component by suction passes above the part camera 64. At this time, the electronic component on the suction nozzle 662*a* is imaged by the part camera 64.

The device pallet 63 is mounted in a front opening of the module 66. The tray unit 67 is disposed in front of the base 65. The tray unit 67 includes a case 670 and a shuttle conveyor 671. A plurality of trays 672 are stacked in the up-down direction in the case 670. The rear end of the shuttle conveyor 671 reaches the upper edge of the device pallet 63. The trays 672 in the case 670 are capable of being drawn rearward (in the direction toward the substrate B) by the shuttle conveyor 671.

The image generating apparatus 1 of the present embodiment is incorporated in the electronic component mounting machine 6. The image generating apparatus 1 includes the lighting apparatus, the mark camera 663, the image processing apparatus 61, and the display apparatus 62 out of the constituent members of the electronic component mounting machine 6.

Electronic components are placed on the trays 672. Each electronic component is transferred by the suction nozzle 662*a* from the tray 672 to the mounting coordinates on the substrate B via the part camera 64. The electronic component is mounted at the mounting coordinates on the substrate B by the suction nozzle 662*a*.

If the orientation of the electronic component placed on the tray 672 is different from the orientation of the electronic component that is mounted on the substrate B, the orientation of the electronic component P1 that is mounted may not match a predetermined orientation. For example, the electronic component P1 may be mounted so as to be rotated 90° or 180° with respect to the predetermined orientation. Thus, the orientation of the electronic component on the tray 672 may be inspected before the orientation inspection is performed in the substrate appearance inspection machine 7 shown in FIG. 2.

In the case of the orientation inspection of the electronic component on the tray 672, the control apparatus 60 performs the operation of the control apparatus 70 shown in FIG. 2, the image processing apparatus 61 performs the operation of the image processing apparatus 4 shown in FIG. 2, and the display apparatus 62 performs the operation of the display apparatus 5 shown in FIG. 2. Moreover, the mark camera 663 shown in FIG. 7 performs the operation of the imaging apparatus 3 shown in FIG. 4, and the lighting apparatus provided together with the mark camera 663 performs the operation of the lighting apparatus 2 shown in FIG. 4. Incorporating the image generating apparatus 1 in the electronic component mounting machine 6 can increase the contrast of the image of the electronic component on the tray 672. Thus, the accuracy of detecting wrong orientation of the electronic component can be increased.

Instead of the mark camera 663, the part camera 64 may be used as the imaging apparatus of the image generating apparatus 1. The lighting apparatus (not shown) provided together with the part camera 64 may be used as the lighting apparatus of the image generating apparatus 1. This can increase the contrast of the image of the electronic component sucked by the suction nozzle 662*a*. Thus, the accuracy of detecting wrong orientation of the electronic component can be increased.

In the above embodiment, white LEDs are used as the light sources 200U, 200M, and 200D, as shown in FIG. 4. However, single-color LEDs of R, G, and B may be used in combination as the light sources 200U, 200M, and 200D. Other illumination units such as a fluorescent lamp may be used. The light sources 200M, 200D need not necessarily have a ring shape (an endless annular shape). For example, the light sources 200M, 200D may have a dot shape or a partial arc shape.

In the above embodiment, as shown in FIG. 4, the three illumination units, namely the epi-illumination unit 20U, the upper oblique-illumination unit 20M, and the lower oblique-illumination unit 20D, are provided in the lighting apparatus 2. However, the number of illumination units is not particularly limited. If the number of illumination units is one, disposing the illumination unit so as to be movable with respect to the imaging apparatus 3 allows the incident angle of the illumination light to be switched as appropriate among θU, θM, and θD.

In the above embodiment, as shown in FIG. 6, the three captured images D1 to D3 are obtained by the imaging apparatus 3 in the selection candidate image generation step. However, the number of captured images D1 to D3 is not particularly limited. The plurality of single-color images D1R, D1G, D1B, D2R, D2G, D2B, D3R, D3G, and D3B can be generated even if the number of captured images D1 to D3 is one.

In the above embodiment, as shown in FIG. 6, the single-color images D1R, D1G, D1B, D2R, D2G, D2B, D3R, D3G, and D3B are generated from the captured images D1 to D3, and the selected image F1R is generated from the single-color images D1R, D1G, D1B, D2R, D2G, D2B, D3R, D3G, and D3B in the before-adjustment image generation step. However, if the number of captured images D1 to D3 is one, the captured image D1 to D3 may be used as it is as the before-adjustment image (the selected image) F1R. This reduces the time required for image processing.

The color components of the single-color images D1R, D1G, D1B, D2R, D2G, D2B, D3R, D3G, and D3B are not particularly limited. The captured images D1 to D3 need not necessarily be color images.

In the above embodiment, as shown in FIG. 6, the single-color images D1R, D1G, D1B, D2R, D2G, D2B, D3R, D3G, and D3B are used as they are as the selection candidate images in the selection candidate image generation step. However, an image obtained by synthesizing the single-color images D1R, D1G, D1B, D2R, D2G, D2B, D3R, D3G, and D3B as appropriate may be used as the selection candidate image. In this case, the single-color images D1R, D1G, D1B, D2R, D2G, D2B, D3R, D3G, and D3B need only be synthesized so as to increase the contrast between the designated area E1 and the comparison area E2 in the selected candidate image. The number of single-color images D1R, D1G, D1B, D2R, D2G, D2B, D3R, D3G, and D3B to be synthesized (how many of the single-color images D1R, D1G, D1B, D2R, D2G, D2B, D3R, D3G, and D3B are synthesized to generate a single selection candidate image) is not particularly limited. Moreover, the number of selection candidate images to be generated is not particularly limited.

In the above embodiment, as shown in FIG. 5, the orientation inspection is performed by using the circular mark M on the electronic component P1. However, the mark M for use in the orientation inspection is not particularly limited. A character, a number, a model number, etc. on the electronic component P2, a semicircular pattern on the electronic component P3, a trapezoidal pattern on the electronic component P4, a quadrangular pattern on the electronic component P5, a linear pattern on the electronic component P6, etc. may be used as the mark M. A shape feature of the electronic component may be used as the mark M.

In the above embodiment, as shown in FIG. 6, the designated area E1 and the comparison area E2 are arranged diagonally. However, the positional relationship between the designated area E1 and the comparison area E2 is not particularly limited. The designated area E1 and the comparison area E2 need only be arranged so as to increase the contrast between the designated area E1 and the comparison area E2.

In the above embodiment, as shown in FIG. 6, the lookup table is created by using the expressions (1) and (2) in the adjusted image generation step. That is, the image modulation (enhancement) is performed by using the expressions (1) and (2). However, the image modulation may be performed by using a modulation expression other than the expressions (1) and (2). The range of the gain value J and the range of the offset value I which are set when creating the lookup table are not particularly limited. Moreover, the increments of the variable x in the expression (2) are not particularly limited.

In the above embodiment, as shown in FIG. 6, the difference in average luminance between the designated area E1 and the comparison area E2 is calculated for each combination of the gain value and the offset value by varying the gain value and the offset value for the adjusted image K1R in the optimal image generation step. However, the increments or decrements of the gain value and the offset value are not particularly limited. If there are a plurality of combinations of the gain value and the offset value that yield the largest difference in average luminance, a combination of the gain value and the offset value that has the smallest gain value need not necessarily be selected.

In the above embodiment, as shown in FIG. 6, the orientation of the electronic component P1 is automatically determined by comparing the average luminance of the designated area E1 with that of the comparison area E2 of the optimal image L1R by the image processing apparatus 4. However, the orientation of the electronic component P1 may be visually determined by the operator by looking at the screen of the display apparatus 5. In this case, the mark M in the optimal image L1R that is displayed on the display apparatus 5 is set to white or black according to the respective average luminance values of the designated area E1 and the comparison area E2. This makes it easier for the operator to determine the orientation of the electronic component P1.

As shown in FIG. 6, in the optimal image generation step, the image processing apparatus 4 may set intermediate luminance (which need not necessarily be a median value) between the average luminance of the designated area E1 and the average luminance of the comparison area E2 of the optimal image L1R as a threshold value. The orientation of the electronic component P1 may be inspected by using this threshold value. In the condition utilization step, this threshold value may be used for the orientation inspection of the subsequent electronic component. The threshold value is conceptually included in the "condition" in the present invention.

In the above embodiment, as shown in FIG. 6, the before-adjustment image generation step (the selection candidate image generation step and the image selection step), the adjusted image generation step, and the optimal image generation step in the image processing method are performed on the first substrate B transferred to the substrate appearance inspection machine 7. However, these steps may be performed outside the substrate production line 9, and the substrate appearance inspection machine 7 may inspect the orientation of the electronic component on the first substrate B transferred thereto, by utilizing the same conditions obtained by these steps. In this case, an imaging environment similar to that of the substrate appearance inspection machine 7, such as that shown in FIG. 4, need be provided outside the substrate production line 9.

In the above embodiment, the control apparatus 70 and the image processing apparatus 4 of the substrate appearance inspection machine 7 are separately disposed. However, the control apparatus 70 and the image processing apparatus 4 of the substrate appearance inspection machine 7 may be integrally disposed by using a common computer or the like. Similarly, the control apparatus 60 and the image processing apparatus 61 of the electronic component mounting machine 6 may be integrally disposed. Although the substrate appearance inspection machine 7 is disposed upstream of the reflow furnace 92 in the above embodiment, the substrate appearance inspection machine 7 may be provided downstream of the reflow furnace 92.

In the above embodiment, as shown in FIG. 5, the orientation inspection is individually performed on the electronic components P1 to P6. However, the orientation inspection may be performed on two or more of the electronic components P1 to P6 at a time by using the imaging apparatus 3 having a large imaging area B1. This reduces the time required for the orientation inspection. In the present embodiment, the image generating apparatus and the image generating method according to the present invention are used for the orientation inspection of the electronic components. However, the image generating apparatus and the image generating method according to the present invention may be used to inspect the electronic components for positional displacement, or to inspect to see if there is any component missing.

What is claimed is:
1. An image generating apparatus used for generating an image for inspecting an orientation of an electronic component mounted on a plurality of substrates of an identical type, the image generating apparatus comprising:
a lighting apparatus that emits illumination light to an imaging area where at least a part of the electronic component is located;
an imaging apparatus that images the imaging area irradiated with the illumination light; and
an image processing apparatus that generates a before-adjustment image based on a captured image obtained by the imaging, generates an adjusted image by adjusting luminance of the before-adjustment image, and generates an optimal image by setting a difference in average luminance between a designated area and a comparison area that is other than the designated area in the adjusted image largest,
wherein
the image processing apparatus combines a plurality of single-color images obtained by decomposing, according to color components, each of a plurality of the captured images obtained from a first one of the substrates to generate the before-adjustment image, generates the adjusted image by adjusting luminance of the before-adjustment image, and generates the optimal image by setting the difference in average luminance between the designated area and the com- parison area that is other than the designated area in the adjusted image largest, and the image processing apparatus generates the optimal image from another one of the captured images obtained from a second or subsequent one of the substrates, by using a condition (including an imaging condition of the captured image) obtained in the course of generating the optimal image from the captured image.

2. The image generating apparatus according to claim 1, wherein
the image processing apparatus generates a plurality of selection candidate images based on a plurality of single-color images obtained by decomposing the captured image according to color components, calculates the difference in average luminance between the designated area and the comparison area for each of the selection candidate images, and selects a selected image having the largest difference in average luminance from all the selection candidate images, and
the before-adjustment image is the selected image.

3. The image generating apparatus according to claim 1, wherein
by using a condition obtained in the course of generating the optimal image from the captured image, the image processing apparatus generates the optimal image from another one of the captured images.

4. The image generating apparatus according to claim 1, wherein
the image processing apparatus generates the adjusted image by adjusting a gain value and an offset value of the before-adjustment image, and
the image processing apparatus generates the optimal image having the largest difference in average luminance, by varying each of the gain value and the offset value of the adjusted image in predetermined increments or decrements and calculating the difference in average luminance between the designated area and the comparison area for each combination of the gain value and the offset value.

5. The image generating apparatus according to claim 1, wherein
the lighting apparatus has a plurality of illumination units,
the plurality of illumination units have different incident angles of the illumination light on the imaging area from each other, and
a plurality of the captured images are obtained by the imaging apparatus for each of the plurality of illumination units.

6. The image generating apparatus according to claim 2, wherein
the plurality of color components are three primary color components of red (R), green (G), and blue (B).

7. The image generating apparatus according to claim 1, wherein
the electronic component has a mark by which an orientation of the electronic component can be determined, and
the mark is included in the imaging area and the designated area.

8. The image generating apparatus according to claim 7, further comprising:
a display apparatus that displays the optimal image, wherein
the image processing apparatus compares the average luminance of the designated area with that of the comparison area of the optimal image before display on the display apparatus, and the image processing apparatus sets the mark of the optimal image to be displayed on the display apparatus to white if the average luminance of the designated area is higher than that of the comparison area, and sets the mark of the optimal image to be displayed on the display apparatus to black if the average luminance of the designated area is lower than that of the comparison area.

9. An image generating method used for generating an image for inspecting an orientation of an electronic component mounted on a plurality of substrates of an identical type, the image generating method comprising the steps of:
generating a before-adjustment image based on a captured image of an imaging area where at least a part of the electronic component is located;
adjusting luminance of the before-adjustment image so as to generate an adjusted image;
setting a difference in average luminance between a designated area and a comparison area that is other than the designated area in the adjusted image largest so as to generate an optimal image;
generating the before-adjustment image by combining a plurality of single-color images obtained by decomposing, according to color components, each of a plurality of the captured images of the imaging area where at least the part of the electronic component is located;
adjusting luminance of the before-adjustment image so as to generate the adjusted image;
setting the difference in average luminance between the designated area and the comparison area that is other than the designated area in the adjusted image largest so as to generate the optimal image; and
using a condition to generate the optimal image from another one of the captured images,
wherein the condition using step is performed on a second or subsequent one of the substrates using a condition (including an imaging condition of the captured image) obtained in performing the before-adjustment image generation step, the adjusted image generation step, and the optimal image generation step on a first one of the substrates.

10. The image generating method according to claim 9, wherein
the before-adjustment image generation step includes the steps of:
decomposing the captured image according to color components to generate a plurality of single-color images, and generating a plurality of selection candidate images based on the plurality of single-color images; and
calculating the difference in average luminance between the designated area and the comparison area for each of the selection candidate images, and selecting a selected image having the largest difference in average luminance from the selection candidate images, and
the before-adjustment image is the selected image.

11. The image generating method according to claim 9, further comprising the step of:
after the optimal image generation step, generating the optimal image from another one of the captured images by using a condition obtained in the course from the before-adjustment image generation step to the optimal image generation step.

12. The image generating method according to claim 9, wherein
in the adjusted image generation step, the adjusted image is generated by adjusting a gain value and an offset value of the before-adjustment image, and in the optimal image generation step, the optimal image having the largest difference in average luminance is generated by varying each of the gain value and the offset value of the adjusted image in predetermined increments or decrements and calculating the difference in average luminance between the designated area and the comparison area for each combination of the gain value and the offset value.

13. The image generating method according to claim 9, wherein the electronic component has a mark by which an orientation of the electronic component can be determined, and the mark is included in the imaging area and the designated area.

14. The image generating method according to claim 13, wherein in the optimal image generation step, the average luminance of the designated area is compared with that of the comparison area in the optimal image, the mark of the optimal image is set to white if the average luminance of the designated area is higher than that of the comparison area, and the mark of the optimal image is set to black if the average luminance of the designated area is lower than that of the comparison area.

* * * * *